(12) United States Patent
Spivey et al.

(10) Patent No.: US 7,291,739 B2
(45) Date of Patent: Nov. 6, 2007

(54) CHIRAL CATALYSTS FOR ASYMMETRIC ACYLATION AND RELATED TRANSFORMATIONS

(75) Inventors: Alan Christopher Spivey, Sheffield (GB); Tomasz Fekner, Lublin (PL)

(73) Assignee: Imperial Innovations Limited, London (GB)

( * ) Notice: Subject to any disclaimer, the term of this patent is extended or adjusted under 35 U.S.C. 154(b) by 450 days.

(21) Appl. No.: 10/754,048

(22) Filed: Jan. 9, 2004

(65) Prior Publication Data

US 2004/0127740 A1  Jul. 1, 2004

Related U.S. Application Data

(62) Division of application No. 10/130,292, filed on May 30, 2002, which is a division of application No. PCT/GB00/04564, filed on Nov. 30, 2000, now Pat. No. 6,743,922.

(30) Foreign Application Priority Data

Nov. 30, 1999 (GB) ................. 9928222.0

(51) Int. Cl.
*C07D 213/04* (2006.01)
*C07D 213/22* (2006.01)
(52) U.S. Cl. ...................... 546/255; 546/257
(58) Field of Classification Search ............ 546/255, 546/257
See application file for complete search history.

(56) References Cited

U.S. PATENT DOCUMENTS 3,306,903 A * 2/1967 Jain et al. ................ 544/360
6,037,479 A  3/2000 Broger et al.

FOREIGN PATENT DOCUMENTS

| EP | 0 889 049 | 1/1999 |
|---|---|---|
| WO | WO9736592 | * 10/1987 |
| WO | 98/22484 | 5/1998 |
| WO | 00/50401 | 8/2000 |

OTHER PUBLICATIONS

Spivey, J Org Chem, vol. 65, pp. 3154-3159, 2000.*
Sammakia, J Org Chem, vol. 64, pp. 4652-4664, 1999.*
Tono-Oka, CA 97:122757, 1982.*
Zemlicka, CA 56:38054, 1961.*
Schreiber et al., "Reactions That Proceed with a Combination of Enantiotopic Group and Diastereotopic Face Selectivity Can Deliver Products with Very High Enantiomeric Excess: Experimental Support of a Mathematical Model", J. Am. Chem. Soc. 1987, 109, 1525-1529.
Brown et al., "Kinetic Resolution Strategies I : Enhanced Product Enantiomeric Excesses and Yields in Sharpless Epoxidations", Tetrahedron: Asymmetry, vol. 2, No. 7, pp. 511-514, 1991.
Evans et al., "Studies Directed Toward the Design of Chiral Acylating Agents. The Utility of chiral N-Benzoylimides in Enantioselective Alcohol Acylation", Tetrahedron Letters, vol. 34, No. 35, pp. 5563-5566, 1993.
Vedejs et al., "Parallel Kinetic Resolution", J. Am. Chem. Soc. 1997, 119, 2584-2585.
Kawabata et al., "Nonenzymatic Kinetic Resolution of Racemic Alcohols through an 'Induced Fit' Process", J. Am. Chem. Soc. 1997, 119, 3169-3170, XP002165380.
Barluenga et al., "Synthesis of Pentasubstituted Pyridines. Cycloadditions of N-Vinylic Heterocumulenes with 1-(N, N-Diethylamine) prop-1-yne.", Tetrahedron, vol. 53, No. 12, pp. 4521-4530, 1997, XP004105513.
Stanforth, "Catalytic Cross-coupling Reactions in Biaryl Syunthesis", Tetrahedron 54, 1998, pp. 263-303.
Roberts, "Preparative biotransformations: the employment of enzymes and whole-cells in synthetic organic chemistry", J. Chem. Soc., Perkin Trans. 1, 1998, pp. 157-169.
Ruble et al., "Kinetic Resolution of Arylalkylcarbinols Catalyzed by a Planar-Chiral Derivative of DMAP: A New Benchmark for Nonenzymatic Acylation", J. Org. Chem., 1998, 63, pp. 2794-2795.
Spivey et al., "Synthesis of Atropisomeric Analogues of DMAP", Tetrahedron Letters vol. 39, No. 48, Nov. 26, 1998, pp. 8919-8922, XP004140965.

(Continued)

*Primary Examiner*—Johann R Richter
*Assistant Examiner*—Lalitha Nagubandi
(74) *Attorney, Agent, or Firm*—Jacobson Holman PLLC

(57) ABSTRACT

A chiral catalyst comprising a 3, 4-disubstituted pyridine, or a salt, N functionalised derivative, dimer or oligomer thereof, wherein the 3-substituent is substantially hindered from rotation about the bond ($sp^2$-$sp^2$ biaryl axis) linking it to pyridine and the 4-substituent is an aliphatic or aromatic amine linked by a single bond to the pyridine, the pyridine nitrogen being functionalised or unfunctionalised, preferably comprising a compound of formula I

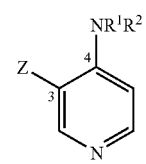

wherein Z is a group substantially hindered from rotation about its bond; and
each of $R^1$ and $R^2$ are independently selected from $C_{1-30}$ alkyl, $C_{3-30}$ cyclo alkyl and/or $C_{3-30}$ aryl, or $NR^1 R^2$ form a cyclic amine; wherein $R^1$ and/or $R^2$ may be optionally substituted and/or include one or more heteroatoms; a composition or support comprising the catalyst; process for the preparation and resolution thereof; process for stereoselective reaction of an optically inactive substrate using the catalyst; and the optically active reaction product thereof.

10 Claims, No Drawings

OTHER PUBLICATIONS

Copeland et al., "Minimal Acylase-Like Peptides. Conformation Control of Absolute Stereospecificity", J. Org. Chem., 1998, vol. 63, pp. 6784-6785.

Dyer et al., "Application of Automation and Thermal Analysis to Resolving Agent Selection", Org. Proc. Res. Dev. 1999, vol. 3, pp. 151-165.

Tao et al., "Nonenzymatic Kinetic Resolution of Propargylic Alcohols by a Planar-Chiral DMAP Derivative: Crystallographic Characterization of the Acylated Catalyst", J. Am. Chem. Soc. 1999, vol. 121, pp. 5091-5092.

Vedejs et al., "2-Aryl-4, 4, 8-trimethyl-2-phosphabicyclo [3.3.0] octanes: Reactive Chiral Phosphine catalysts for Enantioselective Acylation", J. Am. Chem. Soc. 1999, vol. 121, pp. 5813-5814.

Willis, "Enantioselective desymmetrisation", J. Chem. Soc., Perkin Trans. 1, 1999, pp. 1765-1784.

Iwasaki et al., "Nonenzymatic Kinetic Resolution of 1, 2-Diols Catalyzed by an Organotin Compound", Organic Letters, 1999, vol. 1, No. 7, pp. 969-972.

Spivey et al., "Configurationally Stable Biaryl Analogues of 4-(Dimethylamino) pyridine: A Novel Class of Chiral Nucleophilic Catalysts", J. Org. Chem., 1999, vol. 64, pp. 9430-9443, XP000985965.

Campos et al., "A Versatile Synthesis of Pyrrolo-, Furo- and Thienopyridines via Photocyclization of 3-Amino-2-alkene Imines in an Acid Medium", Tetrahedron vol. 55, 1999, pp. 14079-14088, XP004184726.

Spivey et al., "Axially Chiral Analogues of 4-(Dimethylamino) pyridine: Novel Catalysts for Nonenzymatic Enantioselective Acylations", J. Org. Chem., 2000, vol. 65, pp. 3154-3159.

Yin et al., "A Catalytic Asymmetric Suzuki Coupling ro the Synthesis of Axially Chiral Biaryl Compounds", J. Am. Chem. Soc., 2000, vol. 122, pp. 12051-12052.

Sano et al., "Catalytic Asymmetric Acylation of Racemic Secondary Alcohols with Benzoyl Chloride in the Presence of a Chiral Diamine", Chemistry Letters, 1999, pp. 265-266.

* cited by examiner

CHIRAL CATALYSTS FOR ASYMMETRIC ACYLATION AND RELATED TRANSFORMATIONS

This is a Divisional of application application Ser. No. 10/130,292 filed May 30, 2002 now U.S. Pat. No. 6,743,922, which in turn is a 371 of PCT/GB00/04564, filed Nov. 30, 2000.

The present invention relates to a class of novel chiral compounds, a process for the preparation thereof, the use thereof as catalysts, and a process for mediating asymmetric organic transformations therewith. More specifically, the invention relates to a novel class of atropisomeric analogues of 4-aminopyridine, the preparation thereof, the use thereof as catalysts, and a method for performing enantioselective acylation (and related transformations) using the catalyst to preferentially mediate reaction of one enantiomer of an enantiomer pair in a racemic mixture by means of simple—(e.g. H. B. Kagan et al. *Top. Stereochem.* 1988, 18, 249), parallel—(e.g. E. Vedejs et al. *J. Am. Chem. Soc.* 1997, 119, 2584), or dynamic—(e.g. S. Caddick et al. *Chem. Soc. Rev.* 1996, 25, 447) kinetic resolution; or preferentially mediate reaction of one of two enantiotopic functional groups in an achiral meso compound by means of enantioselective desymmetrisation (e.g. M. C. Willis, *J. Chem. Soc., Perkin Trans.* 1 1999, 1765).

Kinetic resolution relies on the fact that one enantiomer of an enantiomer pair in a racemic mixture will react at a faster rate with an enantiomerically enriched chiral reagent or in the presence of an enantiomerically enriched chiral catalyst than the other. Enantioselective desymmetrisation relies on the fact that one of two enantiotopic functional groups in an achiral meso compound will react at a faster rate with an enantiomerically enriched chiral reagent or in the presence of an enantiomerically enriched chiral catalyst than the other.

Enantiomerically enriched reagents and catalysts have enormous potential for the efficient synthesis of enantiomerically highly enriched products such as pharmaceuticals, agrochemicals, fragrances and flavourings, conducting and light emitting polymers and the like. The use of such products in enantiomerically highly enriched form, and preferably as single enantiomers, is significant both for performance reasons and also in some cases to comply with regulatory constraints. Such constraints apply particularly to compounds intended for human or animal consumption or application wherein the desired enantiomer is active and its antipode may be either inert or harmful.

Enantioselective acylation by means of kinetic resolution or enantioselective desymmetrisation is traditionally performed using enzymes. High selectivities (E: 7-1000, wherein E is enzymatic enantioselectivity) have been obtained for selected substrates with specific enzymes (e.g. S. M. Roberts *J. Chem. Soc., Perkin Trans.* 1 1998, 157). However, those enzymes which are compatible with the widest range of substrates (e.g. lipases) are often of low selectivity. Moreover, lipase-mediated acylations can be reversible and undesired equilibria can cause problems. Additionally, enzymes are provided by nature in only one enantiomeric form and are invariably both thermally and mechanically unstable. Furthermore their reactions are usually heterogeneous, only operate efficiently within narrow reaction parameters, are prone to inhibition phenomena, display poor batch-to-batch reproducibility, and consequently are difficult to scale-up.

Recently, chemical methods for mediating enantioselective acylation by means of kinetic resolution or enantioselective desymmetrisation have begun to emerge. Early methods relied on the use of enantiomerically enriched chiral acylating reagents (e.g. D. A. Evans et al. *Tetrahedron Lett.* 1993, 34, 5563) but promising chiral chemical catalysts are now being developed. Chiral chemical catalysts offer some attractive features relative to the use of enzymes. Reactions catalysed in this manner can be rendered irreversible such that no undesired equilibria are present. Chemical catalysts can be made in both enantiomeric forms. Chemical catalysts can be thermally and physically robust. Chemical catalysts can be used under homogeneous conditions. Ideally, they can constitute a tiny fraction of the material to be processed, and can be readily recovered.

The stereoselectivity factor s is the counterpart to enzymatic enantioselectivity, E. Kagan's equation for s for the kinetic resolution of a given substrate (e.g. a secondary alcohol) reacting by pseudo-first order kinetics is given by:

product:

$$s = \frac{\ln[1 - C(1 + ee')]}{\ln[1 - C(1 - ee')]}$$

recovered starting material:

$$s = \frac{\ln[(1 - C)(1 - ee)]}{\ln[(1 - C)(1 + ee)]}$$

where C is the conversion (as a fraction of unity, sum of both reaction enantiomers) while ee and ee' are the enantiomeric excess values of unreacted alcohol and the product, respectively. The enantiomeric excess ee is also referred to as the optical purity; ee is the proportion of (major enantiomer)-(minor enantiomer). For example, a 90% optical purity is 90% ee, i.e., the enantiomer ratio is 95:5, major:minor. Using as an example acylation of a secondary alcohol via kinetic resolution, if s=50, the ee' value of the chiral ester product of kinetic resolution remains above 90% until the conversion exceeds 46%. For example, the unreacted (chiral) alcohol reaches 80% ee at 50% conversion (C=0.5) and 99% ee at 55% conversion. Theoretically, the less reactive alcohol enantiomer could therefore be recovered with 90% efficiency and 99% ee (45% yield based on racemic alcohol).

Impressive selectivities (s: 7-400) have been reported for a number of enantioselective acylation processes by means of kinetic resolution or enantioselective desymmetrisation using a variety of chiral chemical catalysts. Such chiral chemical catalysts are chiral Lewis acids (e.g. F. Iwasaki *Org. Letts.* 1999, 1, 969), chiral phosphines (e.g. E. Vedejs et al. *J. Am. Chem. Soc.* 1999, 121, 5813), chiral diamines (e.g. T. Oriyama et al. *Chem. Lett.* 1999, 265), chiral imidazoles (e.g. S. J. Miller et al. *J. Org. Chem.* 1998, 6, 6784), and chiral 4-aminopyridines (e.g. E. Vedejs et al. *J. Am. Chem. Soc.* 1997, 119, 2584; G. C. Fu et al. *J. Am. Chem. Soc.* 1999, 121, 5091; G. C. Fu et al. *J. Org. Chem.* 1998, 63, 2794; K. Fuji et al. *J. Am. Chem. Soc.* 1997, 119, 3169). All these chiral chemical catalysts except the chiral Lewis acids are believed to operate by nucleophilic catalysis. A possible mechanism of nucleophilic catalysis of acylation of a secondary alcohol mediated by the achiral 4-aminopyridine derivative 4-dimethylaminopyridine (DMAP) is illustrated in Scheme A.

3

Scheme A

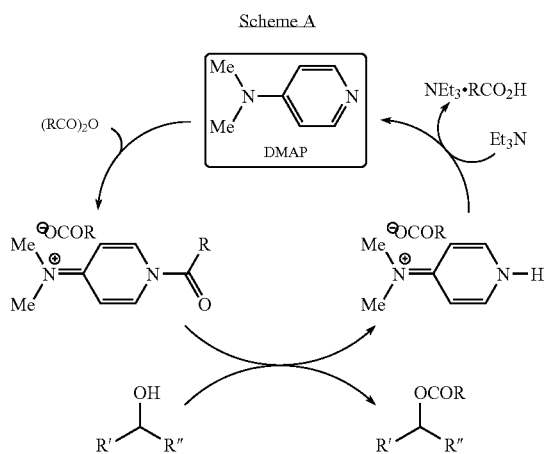
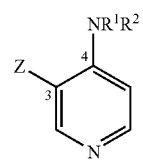

Of the chiral 4-aminopyridine-based catalysts, Fu's planar chiral ferrocenyl chiral 4-aminopyrindine has been shown to be the most versatile (e.g. G. C. Fu et al. *J. Org. Chem.* 1998, 63, 2794). It catalyses a variety of useful enantioselective acylation processes by means of kinetic resolution (e.g. of arylalkylcarbinols with acetic anhydride) via nucleophilic catalysis with excellent selectivity (s: 7-100). However, the published synthesis involves 13 linear steps, has an overall yield of 0.6% from adiponitrile (for the racemate), requires glove-box techniques, and involves chiral stationary phase high-performance liquid chromatography (HPLC) for the final enantiomer separation. Additionally, it is a slow catalyst, typically requiring several days at 0° C. in tert-amyl alcohol to give efficient resolution.

Accordingly, there is a need for enantioselective catalysts which are capable of mediating enantioselective acylation with high selectivity, which can be readily synthesised in high yield and used in low quantities, and which are readily recovered.

We have now found a novel class of catalysts that meet some or all of these needs, specifically provide comparable selectivity, are faster catalysts and are readily prepared, and moreover provide a number of additional advantages. Specifically we have developed a conceptually new class of nucleophilic chiral 4-aminopyridine molecules as catalysts. These molecules possess axial asymmetry as the result of restricted rotation about a highly hindered $sp^2$-$sp^2$ biaryl axis.

In the broadest aspect of the invention there is provided a chiral catalyst comprising a 3,4-disubstituted pyridine, or a salt, N-functionalised derivative, dimer or oligomer thereof, wherein the 3-substituent is substantially hindered from rotation about the bond ($sp^2$-$sp^2$ biaryl axis) linking it to pyridine and the 4-substituent is an aliphatic or aromatic amine linked by a single bond to the pyridine, the pyridine nitrogen being functionalised or unfunctionalised. The catalyst may be provided as its racemic mixture or as only one of its atropisomers.

It is a particular advantage of the invention that the compounds are readily synthesised and resolved. The catalyst is highly active and catalyses rapid reaction.

We have found that with appropriate substitution the atropisomers of the pyridine derivatives of the invention are highly resistant to rotation about the bond at the 3-position, rendering the atropisomers highly resistant to racemisation.

4

Accordingly, in a first aspect of the invention there is provided a catalyst comprising a compound of formula I:

I

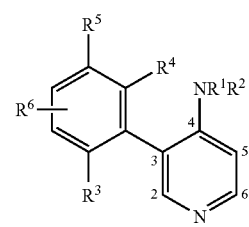

wherein Z is a group substantially hindered from rotation about its bond; and
each of $R^1$ and $R^2$ are independently selected from $C_{1-30}$ alkyl, $C_{3-30}$ cyclo alkyl and/or $C_{3-30}$ aryl, or $NR^1 R^2$ form a cyclic amine; wherein $R^1$ and/or $R^2$ may be optionally substituted and/or include one or more heteroatoms; or
a salt, N-functionalised derivative, dimer or oligomer thereof.

Preferably the pyridine 5-substituent is hydrogen.

A class of 4,5-(fused) substituted compounds is disclosed in A. C. Spivey et al. *Tetrahedron Lett.* 1998, 38, 8919, which studied rates of catalysis. We have now however found that 5-position substitution is detrimental to the efficiency of compounds as asymmetric catalysts, in contrast to the class of compounds of the invention.

More preferably the invention relates to a catalyst comprising a compound of formula II:

II

[Structure II]

wherein $R^1$ and $R^2$ are as hereinbefore defined;
$R^3$ is selected from $C_{1-20}$ alkyl, $C_{3-20}$ cyclo alkyl and/or $C_{3-20}$ aryl, wherein $R^3$ may be optionally substituted and/or include one or more hetero atoms; and
$R^4$ is $C_{1-20}$ alkyl, $C_{3-20}$ cyclo alkyl and/or $C_{3-20}$ aryl or $R^4$ and $R^5$ together are a $C_{3-20}$ fused cyclic or aromatic group wherein $R^4$ or $R^4$ and $R^5$ together may be optionally substituted or include one or more hetero atoms; or
a salt, N-functionalised derivative, dimer or oligomer thereof.

The compounds of formulae I or II as hereinbefore defined may be further substituted or unsubstituted in the pyridine 2- and/or 6-positions and/or in the Z ring. Substituents are independently selected from one or more $R^6$, wherein $R^6$ is selected from for example $C_{1-20}$ alkyl or $C_{3-20}$ aryl, either being optionally substituted or including one or more heteroatoms.

Preferably each of $R^1$ and $R^2$ and $R^3$ independently are selected from: straight or branched chain lower ($C_{1-5}$) or higher ($C_{6-20}$) alkyl, more preferably methyl, ethyl, propyl, butyl, pentyl or hexyl, heptyl, octyl; or from $C_{3-20}$ cyclo alkyl, preferably $C_3C_{14}$ cyclo alkyl; or from $C_{6-24}$ aryl, more preferably an unfused, optionally Spiro 1, 2, 3, 4 or 5 ring alkyl or aryl structure; any of which are optionally substituted and/or include at least one heteroatom; or R$^1$ and R$^2$ together form an optionally substituted cyclo amine, such as

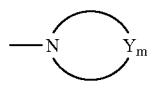

wherein m=1-8 and each Y is independently selected from (CH$_2$)$_n$Y'$_p$ wherein n=1-8, p=0-4 and the sum of n and p is at least 2, and each Y' is independently selected from NR$^7$, O, S, P or Si, preferably Y is (CH$_2$)$_{n'}$, Y' wherein n' is 1-3 or the cyclic amine is

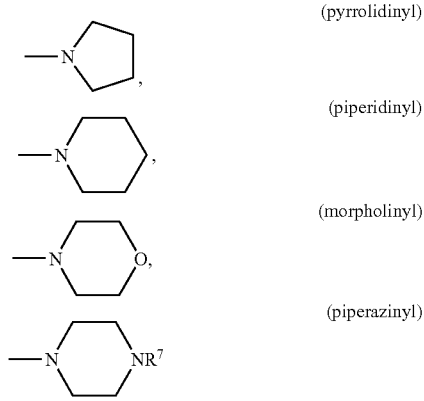

wherein R$^7$ is as hereinbefore defined for R$^1$ or forms a dimer or oligomer of a moiety of compound of formula I:

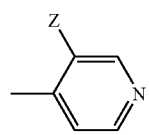

or R$^3$ comprises optionally substituted phenyl or biphenyl, such as optionally substituted (3,5-diphenyl)phenyl, such as [(3',3'',5',5''-tetramethyl)-3,5-diphenyl]phenyl.

Preferably the catalyst as hereinbefore defined is a compound of formula III:

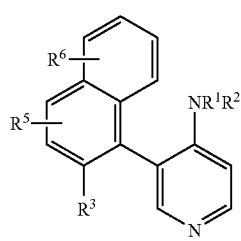

III wherein R$^1$-R$^3$ and R$^6$ are as hereinbefore defined; or a salt, N-functionalised derivative, dimer or oligomer thereof.

Any optional substituents or R$^6$ as hereinbefore defined may be independently selected from any groups that improve or do not detract from performance of the compounds as catalyst.

Suitable substituents include halide, hydroxy, amino, alkoxy, alkyl, cycloalkyl aryl, such as hereinbefore preferably defined for R$^1$, R$^2$ or R$^3$.

Heteroatoms as hereinbefore defined include optionally substituted N, O, S, P, Si.

More preferably, the catalyst as hereinbefore defined is a compound of formula III in which: R$^1$ and R$^2$ are methyl, ethyl, propyl, or butyl; or R$^1$ and R$^2$ together form a pyrrolidinyl-, piperidinyl-, or morpholinyl ring; and R$^3$ comprises a phenyl, 4'-biphenyl, (3,5-diphenyl)phenyl, or [(3',3'',5',5''-tetramethyl)-3,5-diphenyl]phenyl.

Without being limited to this theory it is thought that the compounds of the invention may be rationally designed with respect to the atropisomeric moiety by selection of the group preventing rotation about the pyridine 3-bond, the active catalytic moiety by selection of the amine substituents, and the transformation selective moiety by variation at the pyridine N. Without varying the pyridine N the catalyst is effective for acylation reactions and other transformations for which the high nucleophilicity of this moiety elicits catalytic behaviour whilst the formation of various salts and N-dipolar adducts, for example N-oxide and N-borane adducts, will affect the reactive nature of the N and provide access to other transformations.

In a further aspect of the invention there is provided a composition or a support comprising a catalytically effective amount of a catalyst as hereinbefore defined together with suitable solvent, dilutent and the like or together with a suitable linker on a macromolecule, polymer or a solid support. A supported catalyst may be useful in combinatorial chemistry for conducting plural parallel reaction with labelling and identification of reaction products thereby negating the need for analysis.

In a further aspect of the invention there is provided a compound or formula I, II or III as hereinbefore defined.

In a further aspect of the invention there is provided a process for the preparation of a compound of formula I, II or III as hereinbefore defined comprising cross-coupling a compound of formula IV with an organometal derivative R$^3$-M (Scheme B).

Scheme B

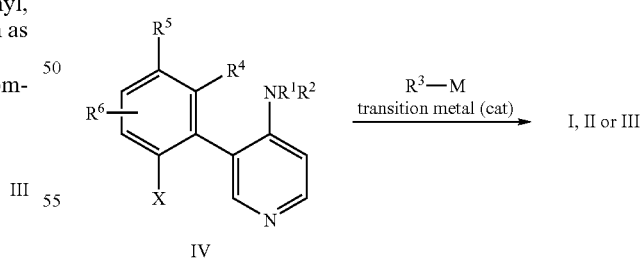

IV

Wherein each R$^6$ independently is hydrogen or is defined as hereinabove, and R$^1$, R$^2$, R$^3$, R$^4$, and R$^5$ are defined as hereinabove and wherein X is a group which is such that, palladium or nickel or a similar transition metal can be oxidatively inserted into the bond between X and the adjacent aryl carbon atom. M is Li, Mg, Zn, Hg, Ti, Al, Zr, Tl, Sn, B and mixtures thereof or a derivative, salt or "ate" complex thereof Preferably, X is a halide, sulfonate, for example trifloxy (OTf), or diazonium salt.

Preferably, the cross-coupling is catalysed by palladium (0) or nickel(0). Preferably, M=MgX, SnR$_3$, or B(OR)$_2$ (i.e. the Kharasch, Stille, and Suzuki cross-coupling protocols respectively, e.g. S. P. Stanforth, *Tetrahedron* 1998, 64, 263).

For example, intermediate IV wherein X=OTf is cross-coupled with an appropriate organo-Grignard derivative (R$^3$-MgBr) in the presence of a catalytic quantity of palladium(0) in a Kharasch-type process.

The product is obtained as a racemic mixture and may subsequently be separated by methods as known in the art, such as by chiral stationary phase HPLC as previously disclosed (A. C. Spivey et al. *Tetrahedron Lett.* 1998, 39, 8919), or preferably by atropisomer-selective transformation with salt formation, enabling resolution. Preferably suitable salt-forming agents are identified by parallel screening as disclosed in "Application of Automation and Thermal Analysis to Resolving Agent Selection", M. B. Mitchell et al. *Org. Proc. Res. Dev.* 1999, 3, 161, using suitable selection of chiral acids in solution of solvents such as ethanol or less polar solvents such as ethyl acetate.

More preferably separation is by atropisomer-selective salt formation using a commercially available chiral acid: (S)-N-tert-butoxycarbonyl-O-benzyl-tyrosine in isopropanol.

Alternatively, the product may be obtained directly from the cross-coupling reaction as a non-racemic mixture by incorporating chiral ligands in the coupling procedure (cf S. L. Buchwald et al. *J. Am Chem. Soc.* 2000, ASAP web release date 11th November), preferably binapthyl ligands.

In a further aspect of the invention there is provided a process for the preparation of an intermediate of formula IV as hereinbefore defined comprising: cross-coupling with concomitant hydrodehalogenation, of an intermediate 4-aminopyridine derivative of formula VI to an arylmetal V; and, for compounds wherein X≠Y, subsequent conversion of group Y into group X by methods known in the art (Scheme C).

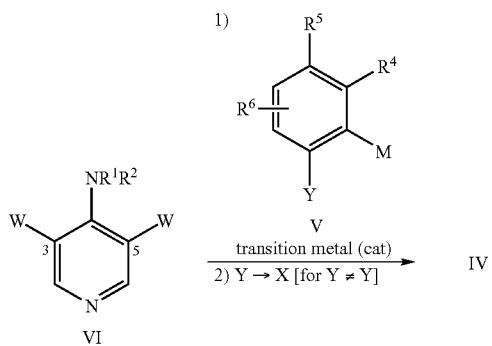

Wherein R$^1$ and R$^2$, and R$^4$, R$^5$, and R$^6$ and M are as hereinbefore defined, W is a halide substituent, and Y is as hitherto defined for X or a substituent of the form OR wherein R is a substituent, known in the art as a protecting group, which allows for conversion to the corresponding compound wherein Y=X by methods known in the art to the corresponding compound wherein Y=OH which is readily converted by methods known in the art to a substituent hitherto defined as X.

Preferably, W is a bromide and Y is a substituent of the form OR wherein R is a protecting group which allows for conversion by hydrogenolysis, as known in the art, to the corresponding phenol wherein Y=OH [e.g. benzyloxy (OBn), or substituted benzyloxy] and transformation of this phenol to an aryl sulfonate (e.g. triflate) suitable for cross-coupling is by methods known in the art (e.g. by reaction with an appropriate sulfonic anhydride, -fluoride or -chloride).

Preferably, the cross-coupling is catalysed by palladium (0). Preferably, M=B(OR)$_2$ (i.e. a Suzuki cross-coupling protocol, e.g. N. Miyaura et al. *Synth. Commun.* 1981, 11, 513) which, under appropriate conditions as known in the art, also effects hydrodehalogenation of the 5-halogen substituent.

For example, intermediate VI wherein W=Br and R$^1$=R$^2$=Et is cross-coupled with an appropriate boronic acid derivative V wherein Y=OBn, and M=B(OH)$_2$ in the presence of a catalytic quantity of palladium(0) in a Suzuki-type process with concomitant 5-hydrodebromination to give, after transformation of Y=OBn to Y=OTf by known methods, intermediate IV.

Utilisation of cross-coupling of 3-halogen-substituted DMAP derivatives with appropriate organo-metal derivatives by analogy to a method previously disclosed (A. C. Spivey et al. *Tetrahedron Lett.* 1998, 38, 8919) can be used to access compounds of structure IV (A. C. Spivey et al. *J. Org. Chem.* 2000, 65, 3154) but this normally high-yielding process gave very poor yields for the class of analogues of the invention (Scheme D).

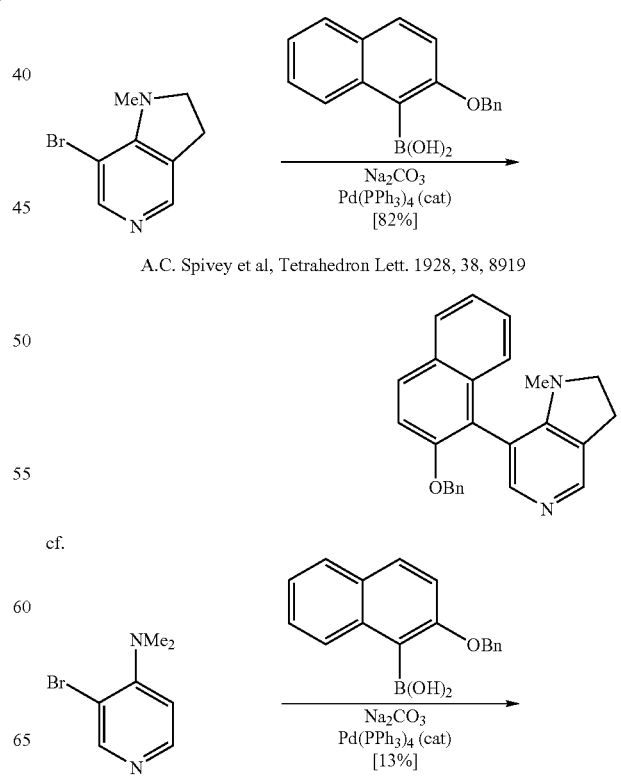

-continued

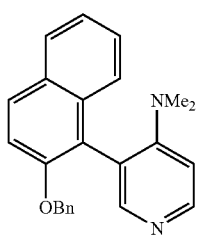

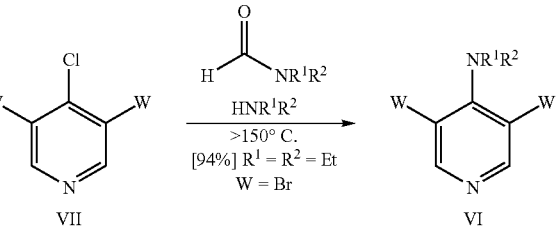

Notwithstanding the possibility that this type of cross-coupling could be optimised, we developed the novel process outlined hithertofore (Scheme C).

The compounds are obtained in excellent yield. The process is also suited for preparation of a range of analogues having different substituents, specifically amine and 3-pyridyl substituents.

The aryl boronate coupling partner V can be obtained commercially or by known means from the appropriate aryl halide, for example as shown in Scheme E, by conversion from commercially available 1-bromo-2-naphthol or an analogue thereof (A. C. Spivey et al. *J. Org. Chem.* 2000, 65, 3154).

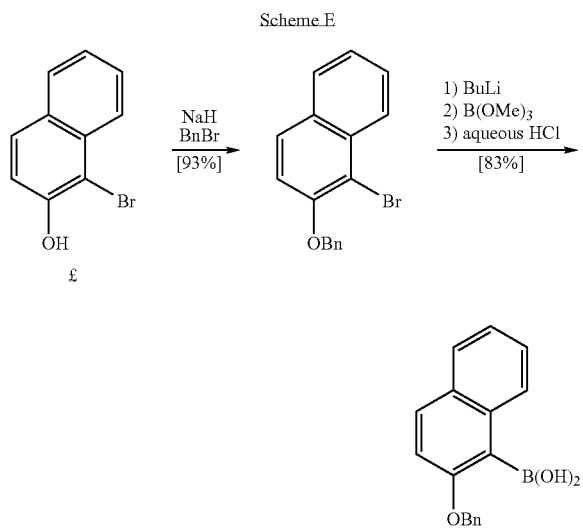

The intermediate 4-aminopyridine derivative of formula VI can be obtained according to the process outlined in Scheme F.

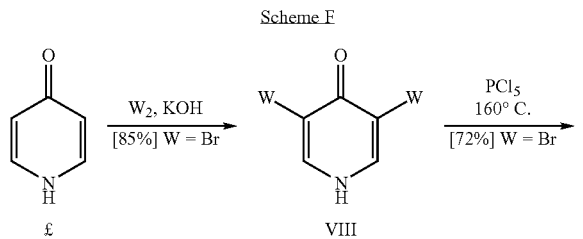

Herein, intermediate 4-aminopyridine derivative of formula VI is obtained from reaction of the trihalopryidine VII with the appropriate secondary amine in the corresponding formamide solvent at elevated temperature. The intermediate trihalopyridine of formula VII is suitably obtained by reaction of the corresponding 3,5-dihalo-4-pyridone of formula VIII with a chlorinating agent. The 3,5-dihalo-4-pyridone of formula VIII is suitably obtained by halogenation of commercially available 4-pyridone.

It is a particular advantage of the invention that the compounds may be prepared simply and conveniently in high yield and conveniently separated into atropisomers illustrated in Scheme G.

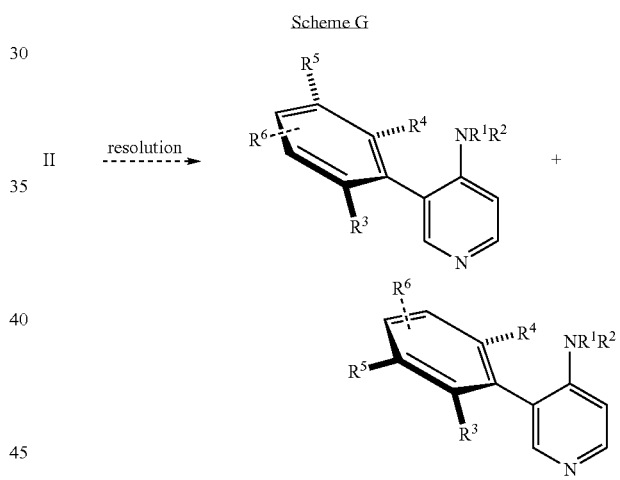

Kinetic parameters were obtained and indicated that an enantiomerically pure sample of suitably highly substituted compounds of the invention would lose much less than 1% of their optical purity over one year in solution at room temperature (A. C. Spivey et al. *J. Org. Chem.* 2000, 65, 3154).

In a further aspect of the invention there is provided a novel intermediate as hereinbefore defined.

In a further aspect of the invention there is provided a catalyst comprising an enantiomer of a compound or formula I, II, or III as hereinbefore defined.

The catalyst is highly active and catalyses rapid reaction.

In a further aspect of the invention there is provided a process for stereoselective reaction of a catalyst of formula I, II, III as hereinbefore defined with an optically inactive substrate to provide one or both enantiomers of a derivative thereof, with simultaneous or subsequent recovery of the catalyst. The invention includes subsequent separation of the product enantiomers.

The reaction may be any suitable reaction that may be catalysed by the catalyst of the invention, including its salts and N-dipolar adducts.

Preferably the process comprises the enantioselective acylation by means of kinetic resolution of e.g. a secondary or tertiary alcohol or primary or secondary amine for which the acylated or further derivative can be industrially useful in enantiomeric form as a pharmaceutical, agrochemical, fragrance, flavouring or as a constituent of a high-value electrically or optically active polymer or the like.

More preferably, the process comprises the reaction of an alcohol of formula IX, wherein $R^8$ and $R^9$ are independently selected from $C_{1-50}$ alkyl, $C_{3-50}$ cyclo alkyl or $C_{3-30}$ aryl, with an acylating agent $R^{10}COU$, wherein $R^{10}$ is optionally substituted $C_{1-15}$ alkyl or $C_{1-12}$ aryl and U is an appropriate leaving group, such as anhydride, under acylating conditions, as known in the art, in the presence of a enantiomerically highly enriched catalyst (preferably≧90% ee) of formula I, II or III as hereinbefore defined, according to Scheme H.

Scheme H

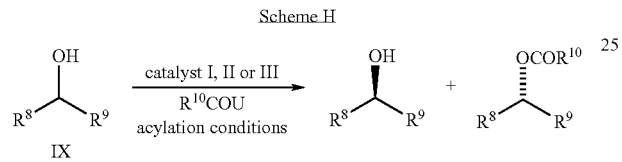

Preferably, the catalyst is enantiomerically enriched such that its ee is ≧98%. More preferably, the catalyst is enantiomerically enriched such that its ee is ≧99%, more preferably ≧99.9%.

Suitable choice of acylating agent, temperature, solvent, and stoichiometric base have been found to improve selectivity of reaction.

The transformation is catalysed with high selectivity (s: 7-500). Selectivities in excess of 50 may be obtained by optimisation. The enantiomeric excess of the products (ee') may be improved, as known in the art, by repeat transformation using the opposite enantiomer of catalyst (i.e. double kinetic resolution: e.g. S. M. Brown et al. *Tetrahedron: Asymmetry* 1991, 2, 511).

Resolution of enantiomers in the process of the invention provides optical purity in excess of 70% preferably in excess of 90% depending on the extent of conversion C.

Alternatively, the process comprises the enantioselective acylation by means of enantioselective desymmetrisation of an achiral meso diol or diamine. The enantioselective reaction of enantiotopic functional groups under acylating conditions in these situations can yield a single enantiomer of the product in yields up to 100%. Additionally, as known in the art, it is usual in such systems that the enantiomeric purity of the monofunctionalised product increases as a function of conversion due to preferential further conversion (i.e. kinetic resolution) of the minor enantiomer into a meso difunctionalised product (i.e. the 'meso-trick': e.g. S. L. Schreiber, et al. *J. Am. Chem. Soc.* 1987, 109, 1525).

Catalyst recovery is suitably 90-100%. Advantageously, catalytic performance is highly reproducible.

The catalyst of the invention may be used in any suitable form and amount. Catalytic amounts of 0.001 to 2 mol %, preferably 0.01 to 0.2 mol %, more preferably 0.05 to 0.15 mol % may be used.

In a further aspect of the invention there is provided a product of a catalytic reaction obtained with use of a catalyst as hereinbefore defined.

The invention is now illustrated in non-limiting manner with reference to the following examples and figures.

EXAMPLE 1

Preparation of a Compound of Formula III 3,5-Bibromo-4-pyridone(VIII, W=Br)

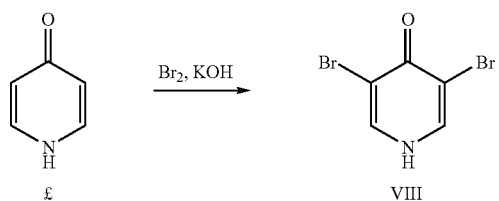

The dibromination of 4-pyridone was carried out according to a modified known method (O. S. Tee et al. *Can. J. Chem.* 1983, 61, 2556). Thus, to an ice-cooled and mechanically stirred solution of 4-pyridone (34.9 g, 0.367 mol) and KOH (41.2 g, 0.736 mol) in water (700 mL) was added $Br_2$ (37.9 mL, 0.735 mol) dropwise over 30 min. After additional 30 min, the white precipitate was filtered off, washed with a copious amount of water, and dried in vacuo to give the crude 3,5-dibromo-4-pyridone (VIII, W=Br) (79.0 g, 85%) which was used in the next step without further purification.

3,5-Dibromo-4-chloropyridine (VII, W=Br)

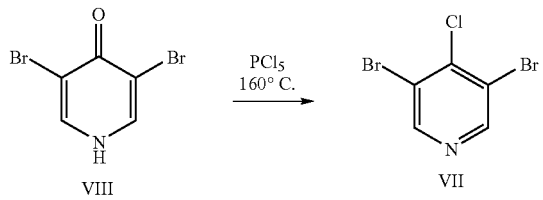

A mixture of 3,5-dibromo-4-pyridone (VIII, W=Br) (79.0 g, 0.312 mol) and $PCl_5$ (79 g, 0.38 mol) was kept at 160° C. for 3 h. The reaction mixture was cooled to 0° C. and quenched by slow addition of water (200 mL). The resulting precipitate was crushed, filtered off, washed with water, and transferred on top of a flash silica column which was subsequently eluted with $CH_2Cl_2$. The crude product thus obtained was crystallised from EtOH to give the title compound, 3,5-dibromo-4-chloropyridine (VII, W=Br) (73.9 g, 72%) as white needles: $R_f$=0.60 ($CH_2Cl_2$); mp 95.0-96.5° C. (EtOH); $^1$H NMR (250 MHz, $CDCl_3$) δ8.65 (s); $^{13}$C NMR (63 MHz, $CDCl_3$) δ121.8, 144.0, and 150.9; IR ($CHCl_3$) $v_{max}$ 1549, 1524, 1410, and 1394 cm$^{-1}$; MS (EI$^+$) m/z (rel intensity) 271 (100%, M$^+$) and 192 (30); HRMS calcd for $C_5H_2Br_2ClN$ (M$^+$) 268.8242. found 268.8231.

3,5-Dibromo-4-(diethylamino)pyridine (VI, $R^1=R^2=Et$, $W=Br$)

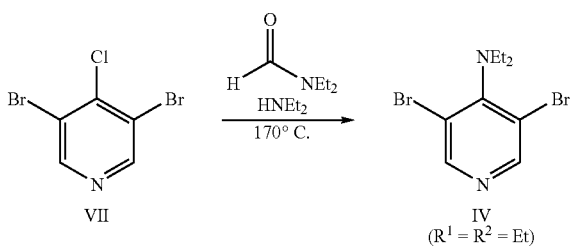

A mixture of trihalopyridine VII (W=Br) (18.8 g, 70.0 mmol), Et$_2$NH (21.7 mL, 0.210 mol), and N,N-diethylformamide (35 mL) was kept in a sealed high-pressure tube at 170° C. for 20 h. The reaction mixture was cooled to room temperature, dissolved in EtOAc (300 mL), and washed with 1M K$_2$CO$_3$ (200 mL) and water (8×200 mL). The organic layer was dried with MgSO$_4$ and evaporated in vacuo to give a brown oil. Purification by flash chromatography (CH$_2$Cl$_2$) gave the title compound, 3,5-dibromo-4-(diethylamino)pyridine (VI, $R^1=R^2=Et$, W=Br), (20.3 g, 94%) as a yellow oil: R$_f$=0.45 (CH$_2$Cl$_2$); $^1$H NMR (250 MHz, CDCl$_3$) δ1.01 (t, J=7.0 Hz, 6H), 3.26 (q, J=7.0 Hz, 4H), and 8.49 (s, 2H); $^{13}$C NMR (63 MHz, CDCl$_3$) δ14.10, 46.05, 122.9, 151.9, and 154.1; IR (CHCl$_3$) ν$_{max}$ 2976, 1553, 1457, 1167 cm$^{-1}$; MS (EI$^+$) m/z (rel intensity) 308 (15%, M$^+$), 193 (100), and 264 (30); HRMS calcd for C$_9$H$_{12}$Br$_2$N$_2$ (M$^+$) 305.9367. found 305.9366.

1-Bromo-2-(phenylmethoxy)naphthalene

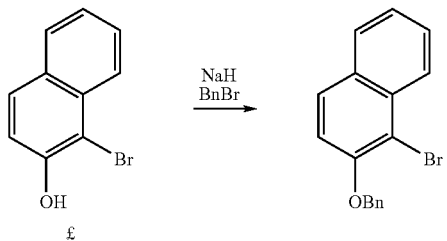

To a suspension of 1-bromo-2-naphthol (15.0 g, 67.3 mmol) and K$_2$CO3 (18.6 g, 135 mmol) in DMF (100 mL) was added benzyl bromide (9.6 mL, 81 mmol) and the mixture was stirred at 60° C. for 5 h. After cooling to room temperature, the solvent was evaporated in vacuo and the residue, dissolved in a small amount of CH$_2$Cl$_2$, passed through a thin pad of flash silica. Fractions containing the product were evaporated in vacuo to give an off-white solid. Crystallisation from CH$_2$Cl$_2$/petrol gave the title compound, 1-bromo-2-(phenylmethoxy)naphthalene, as a white crystalline solid (16.0 g, 76%). The mother liquor was concentrated and purified by flash chromatography (petrol/CH$_2$Cl$_2$, 2/1) to give an additional amount of the product (3.7 g, 17%; total yield: 93%). R$_f$=0.50 (petrol/CH$_2$Cl$_2$, 2/1); mp 104-106° C. (CH$_2$Cl2/petrol); $^1$H NMR (250 MHz, CDCl$_3$) δ5.35 (s, 2H), 7.32 (d, J=9.0 Hz, 1H), 7.38-7.50 (m, 4H), 7.57-7.66 (m, 2H), 7.79-7.86 (m, 3H), and 8.31 (d, J=8.5 Hz, 1H); $^{13}$C NMR (63 MHz, CDCl$_3$) δ71.81, 110.0, 115.6, 124.6, 126.3, 127.2, 127.8, 128.1 (2C), 128.7, 128.9, 130.1, 133.2, 136.7 and 153.0; IR (CHCl$_3$) ν$_{max}$ 1626, 1596, 1502, 1350, and 1268 cm$^{-1}$; MS (EI$^+$) m/z (rel intensity) 314/312 (25%, M$^+$) and 91 (100); HRMS calcd for C$_{17}$H$_{13}$BrO (M$^+$) 312.0150. found 312.0150. Anal. Calcd for C$_{17}$H$_{13}$BrO: C, 65.19; H, 4.18; Br, 25.51. Found: C, 64.94; H, 4.12; Br, 25.71.

2-(Phenylmethoxy)-1-napthaleneboronic Acid (V, $R^4$-$R^5$ fused Aryl Ring, $R^6=H$)

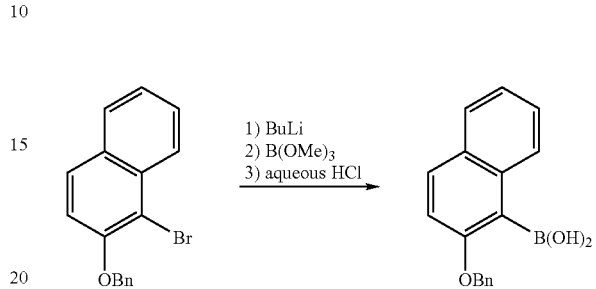

To a suspension of 1-bromo-2-(phenylmethoxy)naphthalene (6.26 g, 20.0 mmol) in Et$_2$O (75 mL) at −78° C. was added n-BuLi (8.0 mL, 2.5 M, 20 mmol) in hexanes and the mixture was stirred at 0° C. for 1 h. After re-cooling to −78° C., the mixture was treated with trimethyl borate (2.5 mL, 22 mmol) and allowed to warm to room temperature overnight. The resulting mixture was quenched with 1M HCl (50 mL) and stirred at room temperature for 45 min. The phases were separated and the extraction was completed with CH$_2$Cl$_2$. The combined organic extracts were dried (MgSO$_4$) and evaporated in vacuo to give the title compound, 2-(pbenylmethoxy)-1-napthaleneboronic acid as a white powder (4.62 g, 83%), which was used in the next step without further purification. For analytical purposes, a small amount of the product was re-crystallised from MeOH/H$_2$O: mp 133.0-135.0° C. (MeOH/H$_2$O); $^1$H NMR (250MHz, d$_4$-MeOH) δ5.20 (s, 2H), 7.28-7.60 (m, 9H), and 7.56-7.88 (m, 2H); $^{13}$C NMR (63 MHz, d$_4$-MeOH) δ71.95, 115.4, 124.8, 127.7 (2C), 128.4, 128.9, 129.5, 129.6, 130.7 (2C?), 131.8, 137.2, 139.0 and 159.7;$^i$ IR (CHCl$_3$) ν$_{max}$ 3609, 3490, 1592, 1509, 1386, and 1332 cm$^{-1}$; MS (EI$^+$) m/z (rel intensity) 278 (10%, M$^+$), 234 (10), and 91 (100); HRMS calcd for C$_{17}$H$_{15}$BO$_3$ (M$^+$) 277.1151. found 277.1163. Anal. Calcd for C$_{17}$H$_{15}$BO$_3$: C, 73.42; H, 5.44. Found: C, 73.07; H, 5.33.

Diethyl{3-[$^2$-(phenylmethoxy)naphthyl](4-pyridyl)}amine (IV, X=OBn, $R^1=R^2=Et$, $R^4$-$R^5$=Fused Aryl Ring, $R^6=H$)

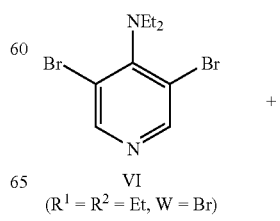

+

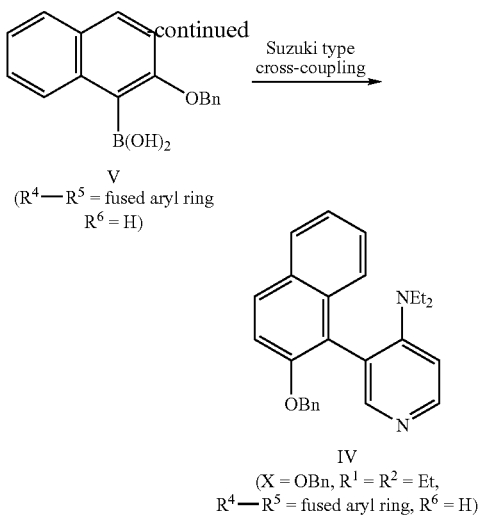

To a solution of aryl dibromide VI (R¹=R²=Et, W=Br) (5.13 g, 16.7 mmol) in toluene (100 mL) and ethanol (5 mL) was added 2M NaOH (30 mL) followed by Pd(PPh₃)₄ (965 mg, 0.835 mmol) and arylboronic acid V (R⁴-R⁵=fused aryl ring, R⁶=H) (5.56 g, 20.0 mmol). The mixture was refluxed for 22 h, cooled to room temperature, and diluted with water (100 mL). The phases were separated and the extraction was completed with CH₂Cl₂. The combined organic extracts were dried (MgSO₄) and evaporated in vacuo to give a brown oil. The residue was purified by flash chromatography (CH₂Cl₂→EtOAc) to give the title compound, diethyl{3-[2-(phenylmethoxy)naphthyl](4-pyridyl)}amine (IV, X=OBn, R¹=R²=Et, R⁴-R⁵=fused aryl ring, R⁶=H), (3.77 g, 59%) as a yellow oil: $R_f$=0.25 (EtOAc); ¹H NMR (250 MHz, CDCl₃) δ0.70 (t, J=7.0 Hz, 6H), 2.85-3.06 (m, 4H), 5.15 (s, 2H), 6.79 (d, J=6.0 Hz, 1H), 7.20-7.44 (m, 9H), 7.75 8.07 (m, 2H), 8.07 (s, 1 H), and 8.31 (d, J=6.0 Hz, 1H); ¹³C NMR (63 MHz, CDCl₃) δ 12.36, 44.83, 70.86, 111.0, 115.0, 120.3, 123.3, 123.9, 125.5, 126.5, 126.8, 127.7, 127.9, 128.4, 129.2, 129.4, 133.2, 137.3, 148.6, 153.1, 153.6, and 5 155.3; IR (CHCl₃) $v_{max}$ 2979, 1587, 1505, and 1271 cm⁻¹; MS (EI⁺) m/z (rel intensity) 382 (15%, M⁺) and 277 (100); HRMS calcd for C₂₆H₂₆N₂O (M⁺) 382.2045. found 382.2041.

1-[4-(Diethylamino)-3-pyridyl]-2-naphthyl (trifluoromethyl)sulfonate (IV, X=OTf, R¹=R²=Et, R⁴-R⁵=Fused Aryl Ring, R⁶=H)

A solution of benzyl ether IV (X=OBn, R¹=R²=Et, R⁴-R⁵=fused aryl ring, R⁶=H) (3.48 g, 9.10 mmol) in EtOH (120 mL) was hydrogenated under normal pressure in the presence of 10% Pd/C (1.0 g) for 9 h (TLC). The reaction mixture was filtered through a thin pad of Celite and evaporated in vacuo to give a crude phenol (2.60 g), which was dissolved in pyridine (30 mL) and treated at 0° C. with Tf₂O (1.70 mL, 10.0 mmol). After 2 h, the solvent was evaporated in vacuo and the residue partitioned between CH₂Cl₂ and water. The phases were separated and the extraction was completed with additional portions of CH₂Cl₂. The combined extracts were dried (MgSO₄) and evaporated in vacuo to give a brown oil. Purification by flash chromatography (CH₂Cl2→EtOAc) gave the title compound, 1-[4-(diethylamino)-3-pyridyl]-2-naphthyl (trifluoromethyl)sulfonate (IV, X=OTf, R¹=R²=Et, R⁴-R⁵=fused aryl ring, R⁶=H), (2.94, 76%) as a yellow oil: $R_f$=0.50 (EtOAc); ¹H NMR (250 MHz, CDCl₃) δ0.77 (t, J=7.0 Hz, 6H), 2.77-3.02 (m, 4H), 6.85 (d, J=6.0 Hz, 1H), 7.45-7.59 (m, 3H), 7.77 (d, J=5.5 Hz, 1H), 7.92-7.95 (m, 2H), 8.14 (s, 1H), and 8.38 (d, J=6.0 Hz, 1H); ¹³C NMR (63 MHz, CDCl₃) δ12.19, 44.87, 112.1, 117.8, 118.3 (q, J=320 Hz), 119.6, 126.5, 127.2, 127.9, 128.4, 129.4, 130.3, 132.7, 132.8, 144.8, 150.1, 153.6, and 155.6; IR (CHCl₃) $v_{max}$ 2978, 1585, 1500, 1421, and 1142 cm⁻¹.

(±)-Diethyl[3-(2-phenylnaphthyl)(4-pyridyl)]amine [(±)-III, R¹=R²=Et, R³=Ph, R⁶=H]

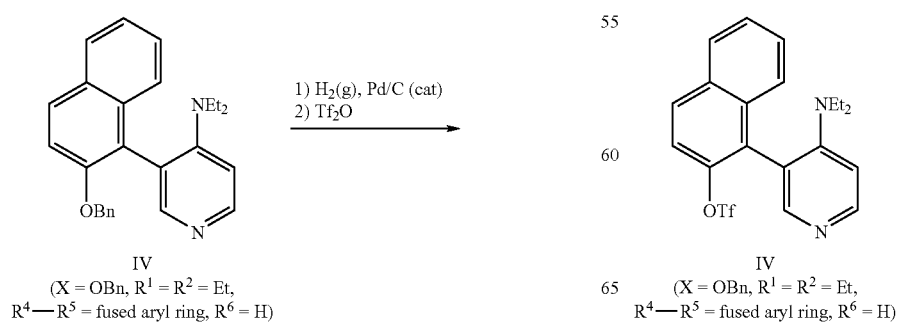

-continued

III
($R^1 = R^2$ = Et, $R^3$ = Ph, $R^6$ = H)

To a solution of triflate IV (X=OTf, $R^1=R^2$=Et, $R^4$-$R^5$=fused aryl ring, $R^6$=H) (193 mg, 0.45 mmol) in $Et_2O$ (3 mL) was added $PdCl_2$(dppp) (13 mg, 22 μmol) followed by PhMgBr (300 μL, 3.0 M, 0.90 mmol) in $Et_2O$. The mixture was refluxed for 16 h, cooled to room temperature, quenched with water (10 mL), and extracted with $CH_2Cl_2$. The combined extracts were dried ($MgSO_4$) and evaporated in vacuo to give a brown oil. Purification by flash chromatography ($CH_2Cl_2$/EtOAc, 3/1→EtOAc) gave the title compound, (±)-diethyl[3-(2-phenylnaphthyl)(4-pyridyl)]amine [(±)-III, $R^1=R^2$=Et, $R^3$=Ph, $R^6$=H], (147 mg, 93%) as a white solid: Rf=0.25 (EtOAc); $^1H$ NMR (250 MHz, $CDCl_3$) δ0.52 (t, J=7.0 Hz, 6H), 2.55-2.88 (m, 4H), 6.50 (d, J=6.0Hz, 1H), 7.09-7.18 (m, 5H), 7.41-7.56 (m, 3H), 7.82-7.94 (m, 3H), 8.18 (s, 1H), and 8.22 (d, J=6.0 Hz, 1H); $^{13}C$ NMR (63 MHz, $CDCl_3$) δ 12.07, 44.56, 111.7, 122.9, 126.0, 126.4, 126.6 (2C), 127.6, 128.1 (2C), 128.6, 129.6, 132.4, 133.1, 134.0, 138.8, 141.7, 148.7, 154.3, and 155.0; IR ($CHCl_3$) $v_{max}$ 2976, 1586, and 1496 $cm^{-1}$.

EXAMPLE A1

Optical Resolution of the Racemic Biaryl [(±)-III, $R^1=R^2$=Et, $R^3$=Ph, $R^6$=H].

The product was resolved according to the following techniques

Method 1—Chiral HPLC

The enantiomers of the biaryl III ($R^1=R^2$=Et, $R^3$=Ph, $R^6$=H) were separated using semi-preparative chiral HPLC (Chiralcel OD column, 1 cm×25 cm; hexanes/EtOAc/$Et_2$NH, 80/19.2/0.8; 4 mL min-1; 30° C.). UV detection was performed at 250 nm. Injections of ~7 mg of the racemate in 70 μL of $CH_2Cl_2$ were made every 12 min. Enantiomer (−)-III was collected from 8.7 to 10.1 min, and the enantiomer (+)-III was collected from 13.3 to 15.9 min. The enantiomer (+)-III was re-purified using the same column (hexanes/EtOAc/$Et_2$NH, 75/24/1; 4 mL min-1; 30° C.) with the product collected from 11.2 to 13.8 min. The enantiomers were further purified by flash chromatography (EtOAc) to give final products as white solids. Analytical chiral HPLC revealed the enantiomeric purity of >99.9% for both the levorotatory $\{[\alpha]^{25}_D$−124 (c 0.58. in $CHCl_3)\}$ and the dextrorotatory $\{[\alpha]^{25}_D$+126 (c 0.57 in $CHCl_3)\}$ enantiomer.

Method 2—Salt Formation: I) Resolving Agent Screen

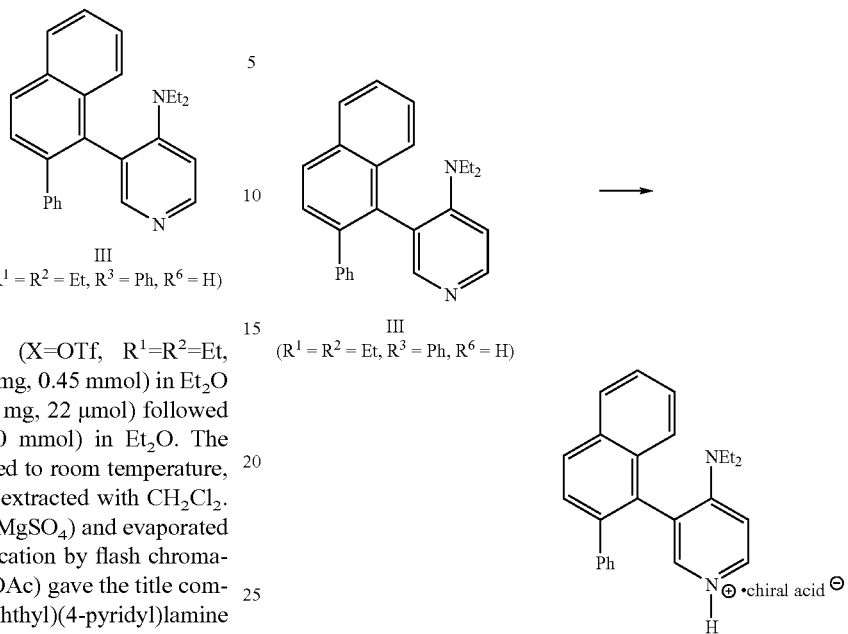

III
($R^1 = R^2$ = Et, $R^3$ = Ph, $R^6$ = H)

Using 480.0 mg (1.362 mmol) of (±)-biaryl III ($R^1=R^2$=Et, $R^3$=Ph, $R^6$=H) and 15.2 ml Ethanol a 0.09 M stock solution of the racemate was prepared.

Apparatus: Using an ACT Chemtech robot, 63×100 μl of this solution was added to 63 wells of a 96 well plate (well positions shown in table). The chiral acid solutions listed below were now added (100 μl) to the indicated well positions. The plate was sealed with a sealing strip, each well cover having a pinhole to allow solvent to escape. The plate was placed in a vacuum oven, under vacuum and at 40° C. overnight.

| Chiral Acid | Well Ref No. |
|---|---|
| (R)-(−)-N-(3,5-DINITROBENZOYL)-ALPHA-PHENYL GLYCINE | H1 101 |
| BOC-O-BENZYL-L-TYROSINE | G1 104 |
| N-CBZ-L-TRYPTOPHAN | F1 105 |
| N-ACETYL-L-TRYPTOPHAN | E1 106 |
| N-ACETYLHYDROXY-L-PROLINE | D1 108 |
| Z-PHE-OH | C1 109 |
| BOC-L-TERT-LEUCINE | B1 110 |
| BOC-L-VALINE | A1 111 |
| Z-L-SERINE | H2 112 |
| DANSYL-L-PHENYLALANINE | G2 113 |
| BOC-MEPHE-OH | F2 114 |
| BOC-N-ME-TYR(2,6-DICHLORO-BZL)-OH | E2 115 |
| Z-D-PYR-OH | D2 117 |
| BOC-TIC-OH | C2 119 |
| Z-GLU(OTBU)-OH | B2 120 |
| (−)-Z-PIPERAZIC ACID | A2 121 |
| N-ACETYL-L-PHENYLALANINE | H3 122 |
| N-(9-FLUORENYLMETHOXY-CARBONYL)-L-TRYPTOPHAN | G3 123 |
| (S)-(+)-2-METHYLBUTYRIC ACID | F3 201 |
| (S)-3-PHENYLBUTYRIC ACID | E3 202 |
| (S)-3-HYDROXYBUTYRIC ACID | D3 203 |
| (S)-(+)-ALPHA-HYDROXY-1,3-DIOXO-2-ISOINDOLINEBUTYRIC ACID | C3 204 |
| 1R-(+)-CAMPHANIC ACID | B3 302 |
| D-CAMPHORIC ACID | A3 303 |
| D-(+)-10-CAMPHORSULFONIC ACID | H4 304 |

-continued

| Chiral Acid | Well | Ref No. |
|---|---|---|
| D-PYROGLUTAMIC ACID | G4 | 401 |
| D-SACCHARIC ACID 1,4-LACTONE | F4 | 402 |
| METHYL(R)-(+)-3-METHYL GLUTARATE | E4 | 404 |
| 2,3:4,6-DI-O-ISOPROPYLIDENE-2-KETO-L-GULONIC ACID | D4 | 405 |
| D-(−)-QUINIC ACID | C4 | 501 |
| L-ALPHA-HYDROXYISOVALERIC ACID | B4 | 502. |
| L-(−)-3-PHENYLLACTIC ACID | A4 | 503 |
| L-MANDELIC ACID | H5 | 505 |
| (R)-4-BROMO MANDELIC ACID | G5 | 506 |
| (R)-4-(3-METHYLPHENYL) MANDELIC ACID | F5 | 507 |
| (R)-4-(2-METHYLPHENYL) MANDELIC ACID | E5 | 508 |
| (R)-4-(4-METHYLPHENYL) MANDELIC ACID | D5 | 509 |
| (R)-4-(3-CHLOROPHENYL) MANDELIC ACID | C5 | 510 |
| (R)-4-PHENYL MANDELIC ACID | B5 | 511 |
| (S)-4-(3-METHOXYPHENYL) MANDELIC ACID | A5 | 512 |
| (S)-4-(4-FLUOROPHIENYL) MANDELIC ACID | H6 | 513 |
| (S)-4-(4-TRIFLUROMETHYLPHENYL) MANDELIC ACID | G6 | 514 |
| BICYCLO[2.2.1]-5-HEPTENE-2-CARBOXYLIC ACID | F6 | 601 |
| MONO-METHYL CIS-5-NORBORNENE-ENDO-2,3-DICARBOXYLATE | E6 | 603 |
| (S)-(+)-KETOPINIC ACID | D6 | 604 |
| (4R)-(−)-2-HYDROXY-5,5-DIMETHYL-4-PHENYL-1,3,2-DIOXAPHOSPHORINANE 2-OXIDE | C6 | 701 |
| (S)-(−)-4-(2-CHLOROPHENYL)-2-HYDROXY-5,5-DIMETHYL-1,3,2-DIOXAPHOSPHORINANE 2-OXIDE | B6 | 702 |
| (R)-(+)-N-(1-PHENYLETHYL)PHTHALAMIC ACID | A6 | 801 |
| 1-METHYL(1S,2R)-(+)-CIS-1,2,3,6-TETRAHYDROPHTHALATE | H7 | 802 |
| (S)-(+)-2-(6-METHOXY-2-NAPHTHYL) PROPIONIC ACID | G7 | 901 |
| (S)-(+)-2-PHENYLPROPIONIC ACID | F7 | 903 |
| (S)-(−)-2-(PHENYLCARBAMOYLOXY) PROPIONIC ACID | E7 | 904 |
| (S)-(−)-2-ACETOXYPROPIONIC ACID | D7 | 905 |
| (R)-(−)-PHENYLSUCCINIC ACID | C7 | 1001 |
| L-MALIC ACID | B7 | 1002 |
| S-METHYLSUCC1NIC ACID | A7 | 1003 |
| (+)-DI-P-TOLUOYL-D-TARTARIC ACID | H8 | 1101 |
| DIBENZOYL-L-TARTARIC ACID | G8 | 1102 |
| D-TARTARIC ACID | F8 | 1103 |
| TRANS 2-(2-METHOXYPHENYL)-5-OXO TETRAHYDROFURAN-3-CARBOXYLIC ACID | E8 | 1203 |
| (S)-(−)-CITRONELLIC ACID | D8 | 1202 |
| (R)-(+)-ALPHA-METHOXY-ALPHA-(TRIFLUOROMETHYL)PHENYLACETIC ACID | C8 | 1201 |
| (R)-4-BROMO MANDELIC ACID | B8 | 506 |

After removing the plate from the oven, well G1 appeared to immediately furnish a solid. After standing for 1 week wells G1, D1, A2, F3, H4, G4, C4, H5 and D7 appeared to be solid. Submitted for microscopical examination and if appropriate DSC analysis.

| Well | Ref | Chiral acid | Microscopy Outcome |
|---|---|---|---|
| C4 | 501 | D-(−)Quinic-Acid | gum/crystal mixture |
| D1 | 108 | N-Acetylhydroxy-L-proline | gum/crystal mixture |
| D7 | 905 | (S)-(−)-2-Acetoxypropionic acid | gum/crystal mixture |
| F3 | 201 | (S)-(+)-2-Methylbutyric acid | gum/crystal mixture |
| G1 | 104 | BOC-O-Benzyl-L-tyrosine | microcrystalline or amorphous |
| G4 | 401 | D-Pyroglutamic acid | mainly crystalline (some gum) |
| H4 | 304 | D-(+)-10-Camphorsulfonic acid | gum/crystal mixture |
| H5 | 505 | L-Mandelic-acid | gum/crystal mixture |
| A2 | 121 | (−)-Cbz-Piperazic acid | not analysed |

DSC of sample G1 comprised two overlapping peaks, suggesting the compound was indeed crystalline and of the eutectic type. The large overlap of peaks did not allow sufficient data to be extracted for eutectic point estimation. Qualitatively though the large peak size for the second peak relative to the first suggested the chiral acid should be a reasonably good resolving agent. Sample G4 also looked like a broad two peak melting endotherm, albeit rather broad and noisy. DSC thermograms of the remaining samples were complex and broad or showed only a single melting endotherm.

Taking all the data together (DSC, crystallization behaviour; and microscopy), N-Boc-O-Benzyl-L-tyrosine was predicted to be a resolving agent for biarly III=($R^1$=$R^2$Et, $R^3$=Ph, $R^6$=H).

Method 2—Salt Formation: II) Resolution

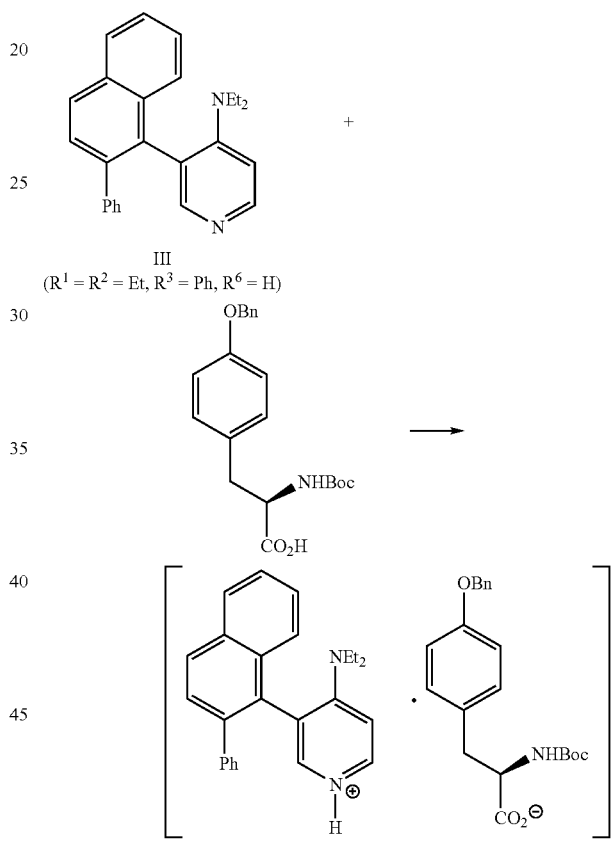

A suspension of (±)-biaryl III ($R^1$=$R^2$=Et, $R^3$=Ph, $R^6$=H) 1.000 g (2.840 mmol) and N-Boc-O-Benzyl-L-tyrosine 1.055 g (2.840 mmol) in isopropanol (9.9 ml) was heated at reflux to furnish a clear solution. Heating was removed and the solution allowed to cool naturally with stirring. After reaching room temperature the solution is left to stir for a further 1 h, then the precipitated solid collected by suction, washing out with the minimum of cold isopropanol (ca 20-30 ml at 5-10° C.). The resulting solid is dried in a vacuum oven at 40° C. overnight to yield the pure salt 0.66 g (32%). NMR of the salt confirmed crystallization of a 1:1 salt. The diastereomeric excess (de) of this salt was >90% as evidenced by Chiral HPLC (conditions as above) with the levorotatory enantiomer of biaryl III being in excess. The mother liquor was similarly enriched in the dextrorotatory enantiomer. Both fractions can be processed to give enantiomerically pure biaryl III (>99.9% ee) by cracking the enriched salts back to the parent amine, followed by a single recrystallization of the parent amine.

FIG. 1 illustrates a corrrelation graph provided for determination of the volume of isopropanol required when using a salt which is initially enriched in one enantiomer. This is useful for instance for obtaining homochiral (+) enantiomer by crystallisation of enriched liquor material with the corresponding D-tyrosine derivative.

EXAMPLE A2

Enantioselective Acylation Using a Catalyst of Formula III

Catalytic kinetic resolution of 1-(1-naphthyl)ethanol (IX, $R^8$=1-naphthyl, $R^9$=Me)

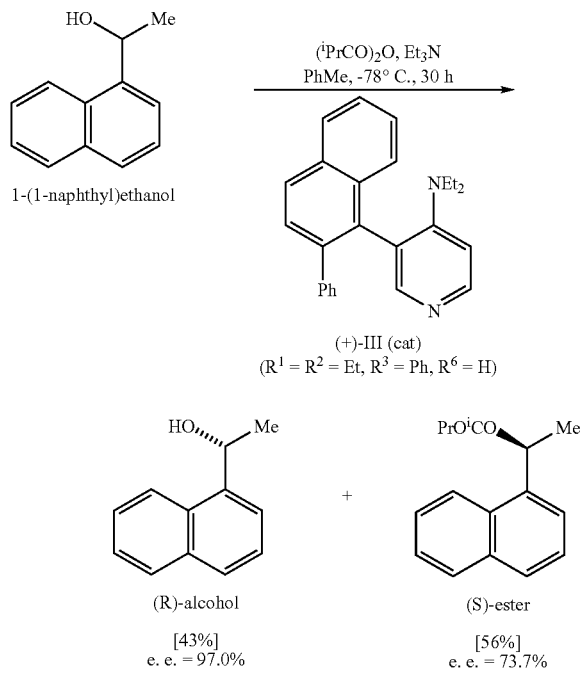

selectivity factor (s): 26.8 at 56.8% conversion
catalyst recovery: 96%; e. e. >99.9%

To a solution of (±)-1-(1-naphthyl)ethanol (2.20 g, 12.8 mmol), triethylamine (1.3 mL, 9.6 mmol) and catalyst (+)-III ($R^1$=$R^2$=Et, $R^3$=Ph, $R^6$=H) (45 mg, 0.13 mmol) in toluene (25 mL) was added dropwise isobutyric anhydride (3.2 mL, 19 mmol) at −78° C. The reaction mixture was stirred at this temperature for 30 h and quenched by slow addition of methanol (10 mL). After additional 15 min at −78° C., the reaction mixture was allowed to warm to room temperature and the solvents were evaporated in vacuo. The residue was dissolved in dichloromethane and washed with 1 M $K_2CO_3$ and brine. The organic layer was concentrated in vacuo and the residue purified by flash chromatography ($CH_2Cl_2$/petroleum ether, 1/1→$CH_2Cl_2$→EtOAc) to give ester (1S)-1-naphthylethyl 2-methylpropanoate (1.73 g, 56%) as a pale yellow oil, alcohol (R)-1-(1-naphthyl)ethanol (956 mg, 43%) as a colourless oil, and catalyst (+)-III ($R^1$=$R^2$=Et, $R^3$=Ph, $R^6$=H) (43 mg, 96%) as a colourless oil. A small sample of ester (1S)-1-naphthylethyl 2-methylpropanoate was hydrolysed with 5% NaOH in MeOH and the resulting alcohol analysed by chiral HPLC (Chiralcel OD; hexanes/2-propanol 90/10, 1 mL min$^{-1}$, 35° C.) which showed enantiomeric excess of 73.7%. Alcohol (R)-1-(1-naphthyl)ethanol was analysed by the same method and its enantiomeric excess was shown to be 97.0%. This corresponds to selectivity factor s=26.8 at 56.8% conversion. The recovered catalyst (+)-III ($R^1$=$R^2$=Et, $R^3$=Ph, $R^6$=H) was shown to retain its optical purity (enantiomeric excess>99.9%) by chiral HPLC analysis (Chiralcel OD; hexanes/ethyl acetate/diethylamine 80/19.2/0.8, 1 mL min$^-$$_1$, 20° C.).

EXAMPLES A2-A13

Catalytic Kinetic Resolutions of Further Secondary Alcohols of Formula IX

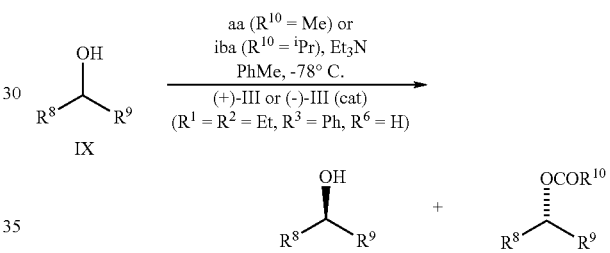

The results are shown in Table 1 were obtained using the following representative experimental procedure (Table 1, Exp A7): A solution of (±)-1-(1-naphthyl)ethanol (172 mg, 1.00 mmol), $Et_3N$ (104 μL, 0.75 mmol), and catalyst (−)-III ($R^1$=$R^2$=Et, $R^3$=Ph, $R^6$=H) (3.5 mg, 10 μmol) in toluene (2.0 mL) was cooled to −78° C. During vigorous stirring, ($^i$PrCO)$_2$O (331 μl, 2.00 mmol) was added dropwise over 3 min. After 2 h at −78° C., ~1 mL of the reaction mixture was removed rapidly via syringe, added to MeOH (2 mL), and stirred at room temperature for 15 min. The solvents were then evaporated in vacuo and the alcohol and ester were separated by flash chromatography (petroleum ether/ $CH_2Cl_2$→$CH_2Cl_2$). After 504 min, the reminder of the reaction was quenched by the dropwise addition of MeOH (3 mL) over 2 min. After 15 min at −78° C. and 15 min at room temperature, the solvents were evaporated in vacuo and the alcohol and ester were separated as described above. The esters obtained from the two aliquots were hydrolysed by heating to reflux in 5% NaOH/MeOH (2 mL) for 5 min. After evaporation of the solvent, the residue was passed through a short flash silica column eluted with EtOAc. The enantiomeric excess for the unreacted alcohols and the alcohols obtained by the ester saponification was established by analytical chiral HPLC (Chiralcel OD column, 1 cm×25 cm hexanes/2-propanol, 90/10; 1 mL min$^{-1}$; 30° C.). The results are given in Table 1 (Exp A7).

TABLE 1

| Exp | $R^8$ | $R^9$ | Acylating Agent (equiv) | Time (min) | Ee (alcohol) | Ee (ester) | Conversion C (%) | Selectivity s (%) |
|---|---|---|---|---|---|---|---|---|
| A2 | 1-naphthyl | Me | aa (2.0) | 120 | 14.16 | 77.09 | 15.52 | 8.88 |
|   |   |   |   | 504 | 46.57 | 69.91 | 39.98 | 8.87 |
| A3 | 1-naphthyl | Me | aa (0.75) | 120 | 4.87 | 80.46 | 5.71 | 9.69 |
|   |   |   |   | 437 | 17.53 | 77.37 | 18.47 | 9.30 |
| A4 | 1-naphthyl | Me | aa (0.75) | 120 | 18.63 | 69.47 | 21.15 | 6.65 |
|   |   |   |   | 379 | 43.05 | 63.7 | 40.33 | 6.82 |
| A5 | 1-naphthyl | Me | aa (0.75) | 120 | 5.09 | 79.5 | 6.02 | 9.21 |
|   |   |   |   | 456 | 14.56 | 77.12 | 15.88 | 8.92 |
| A6 | 1-naphthyl | Me | aa (0.75) | 120 | 2.87 | 74.72 | 3.70 | 7.11 |
|   |   |   |   | 617 | 10.17 | 72.95 | 12.24 | 7.06 |
| A7 | 1-naphthyl | Me | iba (2.0) | 120 | 18.56 | 89.33 | 17.20 | 21.27 |
|   |   |   |   | 504 | 62.37 | 83.64 | 42.72 | 21.18 |
| A8 | Ph | Me | iba (2.0) | 456 | 49.89 | 78.13 | 38.97 | 13.30 |
| A9 | Ph | Et | iba (2.0) | 580 | 43.07 | 79.15 | 35.24 | 13.08. |
| A10 | Ph | isoPr | iba (2.0) | 606 | 44.46 | 66.52 | 40.06 | 7.64 |
| A11 | Ph | tertBu | iba (2.0) | 631 | 18.78 | 88.78 | 17.46 | 20.21 |
| A12 | Ph | isoPr | iba (2.0) | 606 | 29.8 | 72.69 | 29.08 | 8.43 |
| A13 | 1-naphthyl | Me | iba (1.0) | 480 | 26.28 | 91.38 | 22.34 | 28.69 | aa = acetic anhydride,
iba-isobutyric anhydride

Further advantages of the invention are apparent from the foregoing.

The invention claimed is:

1. A process for stereoselective reaction of a catalyst selected from the group consisting of formula I:

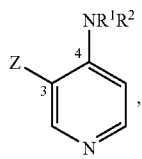

wherein the 3-substituent Z is substantially hindered from rotation about the bond (sp$^2$-sp$^2$ biaryl axis) linking it to pyridine, and wherein each of $R^1$ and $R^2$ are independently selected from the group consisting of $C_{1-30}$ alkyl, $C_{3-30}$ cyclo alkyl and/or $C_{3-30}$ aryl, or $NR^1 R^2$ form a cyclic amine; wherein $R^1$ and/or $R^2$ may be optionally substituted and/or include one or more heteroatoms;

formula II:

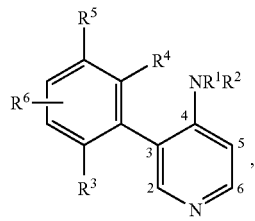

wherein $R^1$ and $R^2$ are as hereinbefore defined;
$R^3$ is selected from the group consisting of $C_{1-20}$ alkyl, $C_{3-20}$ cyclo alkyl and/or $C_{3-20}$ aryl, wherein $R^3$ may be optionally substituted and/or include one or more hetero atoms;
$R^4$ is $C_{1-20}$ alkyl, $C_{3-20}$ cyclo alkyl and/or $C_{3-20}$ aryl or $R^4$ and $R^5$ together are a $C_{3-20}$ fused cyclic or aromatic group wherein $R^4$ or $R^4$ and $R^5$ together may be optionally substituted or include one or more hetero atoms; and
one or more $R^6$ are each independently selected from the group consisting of $C_{1-20}$ and $C_{3-20}$ aryl, optionally substituted and/or including one or more hetero atoms;
or formula III:

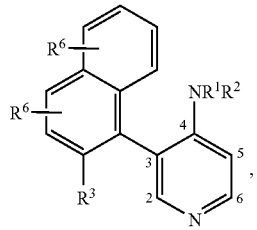

wherein $R^1$-$R^3$ and $R^6$ are as hereinbefore defined; or a salt, dimer or oligomer thereof;
with an optically inactive substrate to provide one or both enantiomers of a derivative thereof, with simultaneous or subsequent recovery of the catalyst.

2. The process as claimed in claim 1, which comprises the enantioselective acylation by means of kinetic resolution of a secondary alcohol.

3. The process as claimed in claim 1, which comprises the reaction of an alcohol of formula IX:

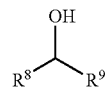

wherein $R^8$ and $R^9$ are independently selected from $C_{1-50}$ alkyl, $C_{3-50}$ cycloalkyl or $C_{3-30}$ aryl, with an acylating agent $R^{10}COU$, wherein $R^{10}$ is optionally substituted $C_{1-15}$ alkyl or $C_{1-12}$ aryl and U is an appropriate leaving group, such as anhydride, under acylating conditions in the presence of a enantiomerically highly enriched catalyst selected from the group consisting of formula I:

formula II:

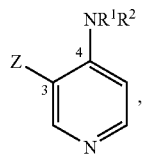

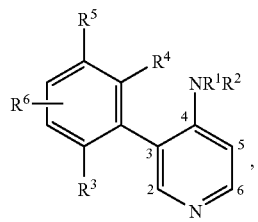

or formula III:

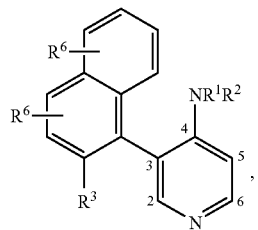

according to Scheme H,

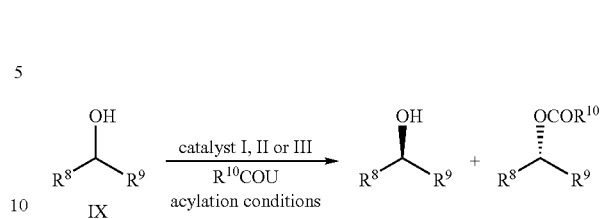

4. The process as claimed in claim 1, in which catalytic amounts of 0.001 to 2 mol %, are used.

5. The process as claimed in claim 1, in which catalytic amounts of 0.001 mol % to 0.2 mol %, are used.

6. The process as claimed in claim 1, in which catalytic amounts of 0.05 to 0.15 mol % are used.

7. The process as claimed in claim 1, in which catalytic amounts of 0.05 to 0.2 mol % are used.

8. The process as claimed in claim 1, which comprises the enantioselective acylation by means of kinetic resolution of tertiary alcohol.

9. The process as claimed in claim 1, which comprises the enantioselective acylation by means of kinetic resolution of a primary amine.

10. The process as claimed in claim 1, which comprises the enantioselective acylation by means of kinetic resolution of a secondary amine.

* * * * *